Figure 1:
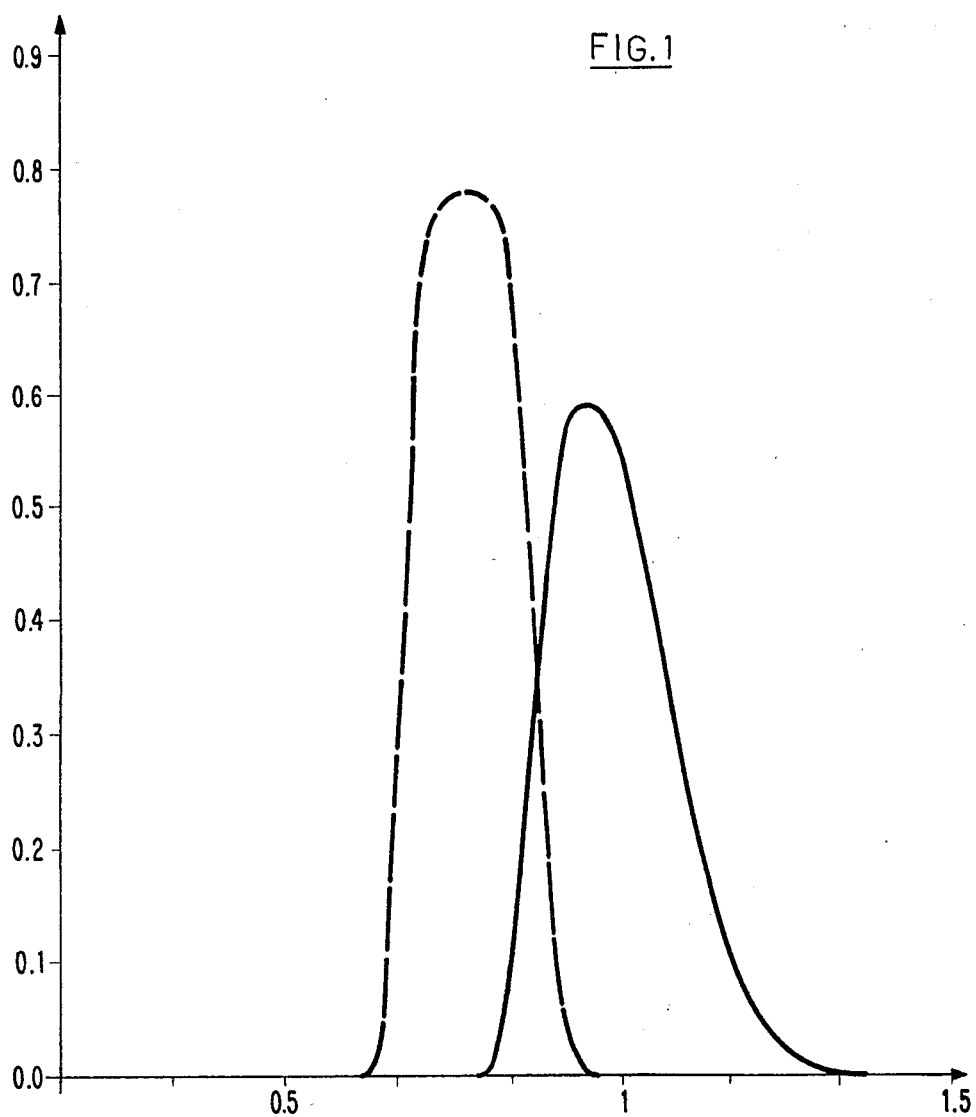

United States Patent [19]
Niederjaufner et al.

[11] Patent Number: 4,795,839
[45] Date of Patent: Jan. 3, 1989

[54] PROCESS FOR SEPARATING MIXED MONOCHLOROTOLUENE ISOMERS, A PLANT FOR CARRYING OUT THE PROCESS, AND THE ISOMERS SEPARATED IN THIS MANNER

[75] Inventors: Guido Niederjaufner; Achille Pontoglio, both of Brescia; Giuseppe Storti, Lodi; Massimo Morbidelli; Sergio Carra' , both of Milan, all of Italy

[73] Assignee: CAFFARO S.p.A. Societa per l'Industria Chimica ed Elettrochimica, Milan, Italy

[21] Appl. No.: 514,264

[22] Filed: Jul. 15, 1983

[30] Foreign Application Priority Data
Jul. 15, 1982 [IT] Italy ................. 22405 A/82

[51] Int. Cl.$^4$ ............................... C07C 17/38
[52] U.S. Cl. ................................... 570/211
[58] Field of Search ........................... 570/211

[56] References Cited

U.S. PATENT DOCUMENTS 2,958,708 11/1960 Flick et al. .............. 570/211
4,254,062 3/1981 Wambach et al. ......... 570/211

FOREIGN PATENT DOCUMENTS 0046068 2/1982 European Pat. Off. ........ 574/211
25089 2/1982 Japan ..................... 570/211

Primary Examiner—Werren B. Lone
Attorney, Agent, or Firm—Stevens, Davis, Miller & Mosher

[57] ABSTRACT

The invention relates to a process for separating mixed monochlorotoluene isomers, which comprises a first stage of adsorption carried out by passing said mixture through at least one column filled with a zeolite, and a second stage of deadsorption from said zeolite carried out by passing two deadsorbents in succession in the vapor phase through the column.

3 Claims, 3 Drawing Sheets

PROCESS FOR SEPARATING MIXED MONOCHLOROTOLUENE ISOMERS, A PLANT FOR CARRYING OUT THE PROCESS, AND THE ISOMERS SEPARATED IN THIS MANNER

Generally, because of the complexity of the necessary processes and plants, the separation of compounds having very close chemical and physical properties, such as isomer mixtures, is one of the most difficult problems of industrial practice. In particular, with regard to the present invention, the availability of parachlorotoluene and orthochlorotoluene of high purity in excess of 99 weight % is very desirable industrially, for use as raw material in secondary chemical synthesis. However, in the synthesis of monochlorotoluene, for example by chlorination of the aromatic ring, the formation of a mixture of orthochlorotoluene and parachlorotoluene is inevitable even in the presence of a catalyst, their relative quantities depending on the type of catalysis.

However, the metachlorotoluene isomer forms in negligible quantity (about 0.3%).

The separation of the orthochlorotoluene and parachlorotoluene isomers is very difficult to carry out industrially, because of the closeness of their boiling points (3° C.), and because of the similarity of the other chemical and physical characteristics. In the most commonly used method, the orthochlorotoluene is separated by superfractionation with a very large number of theoretical stages, whereas the para isomer can be separated by fractional crystallisation, although this presents considerable problems because of the formation of eutectic mixtures, and the number of stages required. The combined use of the two aforesaid methods is also known.

The difficulties connected with these known separation methods are apparent. In particular, the superfractionation requires excessively complicated and costly plant.

One object of the present invention is to separate mixed monochlorotoluene isomers by a process which is considerably more simple and convenient than those proposed by the aforesaid known art, and thus substantially more economical.

In this respect, it should be noted that separation methods have been recently developed based on selective adsorption on solids such as activated carbon and zeolite materials.

Of those patents relating to separation by these methods, mainly regarding the separation of n-paraffins from branched paraffins and the separation of substituted aromatic isomers, U.S. Pat. No. 2,958,708 deals very generally with the interaction between mono and dihalo substituted isomers with certain zeolites.

In order to better understand the invention, some general concepts regarding known separation methods utilising fluid-porous solid interactions will be discussed.

Generally, a quantity of solid, normally granular, is brought into contact with the fluid mixture to be separated into its individual constituents, to form a liquid phase richer in the less adsorbable components and a solid phase which incorporates the more selectively adsorbed components, which can then be extracted for example by elution with a solvent or by changing the operating temperature and pressure variables.

It is known to operate in a succession of equilibrium stages by reiterating the described elementary operation, with stages physically separated in different vessels, either with movement of solid, or with solid in a fixed bed.

Recently, as an improvement on the prior art, the sequence of adsorption and elution stages has been carried out in a fixed bed by feeding the mixture to be separated or the eluent and drawing off the purified product at suitable flow rates and positions along the column, so as to render the concentration profile for the individual components stationary within the column.

In order to recover the phase retained in the solid, it is eluted according to the known art by a solvent or diluent which does not interact with the absorbed component, or interacts only negligibly under the operating conditions, and certainly not as to be competitive with the individual components to be separated, i.e. not to become absorbed.

It is known that the behaviour of the individual component between the external fluid phase and the absorbed phase can be described under equilibrium conditions by means of isotherm curves which are generally non-linear for separation problems. These curves, besides expressing the distribution between the solid phase and fluid phase at all points, contain other information such as the loading on the solid corresponding to saturation (at the indicated temperature and pressure), which hereinafter will be indicated by the symbol $\Gamma_i{}^\infty$ and expressed in moles of the $i^{th}$ component per gram of anhydrous solid, and also the quality of the bond which is expressed by the value of an equilibrium constant, hereinafter indicated by the symbol $Keq_i$ in liters/mole, this being the ratio of the kinetic constants, again at the indicated temperature, for the absorption process and the deadsorption process. High values of this constant indicate considerable ease of adsorption.

It is also known they many of the adsorbed components simultaneously present interact to make the operation competitive. In other words, the quantity of the individual component present in the solid under equilibrium conditions depends, in a considerably non-linear manner, on the concentration of all the elements present and on the value of the specific $Keq_i$ constants for the previously described component-solid binary interaction.

The interaction cannot therefore be considered as the simple removal of those various components which have greater affinity for the solid, but rather a competition between them, which cannot be described in terms of linearised equilibrium.

The fluid used for extracting the adsorbed component from the solid can interact with said component either strongly or weakly, i.e. either competitively or negligibly with respect to the components to be separated. In the first case (strong interaction), the value of its equilibrium constant as heretofore defined will be either comparable with, i.e. of the same order of magnitude, or higher than the value of the constant for the components to be separated. In the second case (weak interaction) the value of its equilibrium constant is negligible or in any case less than the value of the constant for the components to be separated, as will be described hereinafter.

Hereinafter, a fluid having interaction of the first type will be known as a deadsorbent, whereas a fluid having interaction of the second type will be known as a solvent, diluent or eluent.

The considerable difference must be emphasised between the two types of extractors, in the first case there being competition towards the solid, with the substitution of components in selective cavities of the solid. In the second case, this is either only mildly present or is completely absent and in any case quite negligible.

In the first case, the absorbed component is extracted by competition, while in the second case it is eluted into an inert phase and extracted by concentration difference between the adsorbed phase and external phase. In this case, it is more correct to speak of elution.

The total void space available for the fluid phase can be divided into two sections, of which only the internal porosity representing the interstitial volume is selective and useful for separation purposes. The external void space, being the free space between the solid particles, is not selective and as it requires a large quantity of material for filling, does not enable high liquid phase final concentrations of the individual separated components in the deadsorbent or diluent to be obtained. As the components must be separated from these latter by known methods, for example distillation, increased dilution leads to increased process costs. In order to reduce them, the known art teaches the use of a diluent which does not interact in the adsorption process, this being fed after the deadsorbent in order to expel the deadsorbent-deadsorbed component mixture from the external cavities, i.e. from the external void space of the solid. The higher concentrations obtainable can compensate for the increased process complication.

It should be emphasised that according to this method, the second fluid, the eluent, serves only to expel from the vessel the matter which has accumulated in the external void space between the solid particles, thus washing the bed.

According to the known art, in order to separate any mixture, for example a binary mixture, the mixture to be separated and the extractor fluid are fed in cyclic succession to one end of a bed composed of granular adsorption material, with flow rates and for times such as to obtain enrichment in the required compounds. These beds can be connected together in order to process a continuous throughput. The succession, the flow rates and cycle duration are obviously related, for a fixed quantity of material to be treated and for a fixed final purity, to the form of the equilibrium relationship of the individual components, in particular whether they can be correlated by Langmuir relationships, and to the values of the equilibrium constants, this being valid without prejudicing the generalities of the problem. If the extractor fluid is a deadsorbent, the known art teaches that the operation should be carried out in such a manner as to obtain migrating concentration pulses in the column.

The importance assumed by the deadsorbent is clear, its behavior, in particular its load at saturation and its equilibrium constant together with its facility for subsequent separation by known methods, completely defining the type of operation, the cycle duration, the percentage recoverable for each bed, the number of beds necessary for completing the operation, the concentration of useful product and the possibility of recycling a non-separated section.

Let us assume that a multi-component mixture, which for simplicity of description will be taken as binary containing two substances A and B, is to be separated. If A and B are fed for a short time through the absorbent bed, this will become saturated preferentially with one of the two substances, for example B, while A will remain preferentially external to the adsorbent material.

If a deadsorbent stream, D, is then fed, then its composition at the plant outlet will be of the following type: in a time a−b, A−D is obtained; in a time c−d, B+D is obtained; whereas in a time b−c, a mixture A+B+D is obtained, and this is recycled. Assuming that the nature of the chosen deadsorbent D is such as to allow its subsequent easy separation both from A and from B by known low-cost methods, the industrial process consists of repeating the described separation cycle, which can operate either in the liquid phase or in the vapour phase.

In the specific case of monochlorotoluene, it has been found that if a single deadsorbent D is used, which may be a single compound or more compounds in mixture, the progress of the separation of the aforesaid type is unsatisfactory due to low plant yield, the plant being of too high dimensions and high operating costs. In this regard the EP-A- No. 0046068 can be cited.

Further objects of the invention, related specifically to the solution of the aforesaid problems are consequently to provide complete separation of the mixed monochloro toluene components, i.e. total component recovery, with a component purity which is not less than 99%, this being attained with high plant yield and low operating costs.

According to the invention the aforesaid objects are attained by a process for separating mixed monochlorotoluene isomers, comprising a first stage of adsorption carried out by passing said mixture through at least one column filled with a zeolite, characterized by comprising a second stage of deadsorption from said zeolite carried out by passing two deadsorbents in succession in the vapour phase through the column.

More particularly, according to the preferred embodiments of the present invention, the monochlorotoluene isomers are separated by vapour phase adsorption on wide pore zeolite materials, such as type CaX and KY faujasites, at a temperature of between 150° and 350° C. (preferably between 180° and 250° C.) at a pressure of between 0 and 5 atmospheres (preferably between 0.8 and 1.5 atm.), by feeding the orthochlorotoluene+parachlorotoluene mixture and two deadsorbents in the form of toluene and monochlorobenzene through a bed of solid in cyclic sequence. It should be noted that the two deadsorbents interact with the solid with the same mechanism, they having their equilibrium constants lying within the limits indicated hereinafter, these contacts being obtained from interpretation of the break-through curves as reported in the following examples. Deadsorption takes place by competition rather than by elution of the matter retained in the solid by a solvent.

According to the invention, it is preferable to use zeolite X in which the cation present has been exchanged with calcium to the extent of more than 98%, and zeolite Y in which the cation present has been exchanged with potassium to the extent of more than 98%.

The isomer metachlorotoluene in binary mixture with the other isomers also has break-through curves and specific parameters analogous to those of the isomers orthochlorotoluene and parachlorotoluene. If it is present in non-negligible quantity in the starting mixture, its separation occurs without deviating substantially from that described with respect to the other isomers.

The separation capacity of the mixtures used according to the invention was evaluated by expressing the selectivity as:

$$a_{p/o} = \frac{\Gamma_p C_o}{\Gamma_p C_p}$$

(where $\Gamma_p$ is the quantity of parachlorotoluene adsorbed in moles/g of zeolite, $\Gamma_o$ is the quantity of orthochlorotoluene adsorbed in moles/g of zeolite, $C_o$ is the orthochlorotoluene concentration in the fluid phase in moles/liter at equilibrium, $C_p$ is the parachlorotoluene concentration in the fluid phase in moles/liter at equilibrium).

Selectivity in the liquid phase was measured by bringing a known volume of ortho and parachlorotoluene solution in n-octane or other diluent solvents, into contact with known quantities of zeolite for the time necessary to reach equilibrium, and measuring the consequent variation in the concentration of the two components. Selectivity in the vapour phase was evaluated by interpreting break-through curves such as those reported in the examples given hereinafter. Table 1 shows as an example the selectivity ranges obtained at ambient temperature for variously exchanged Y zeolites. Table 2 shows as an example some selectivity data obtained for variously exchanged X zeolites, again at ambient temperature.

TABLE 1

Selectivity ranges at ambient temperature for variously exchanged Y zeolites.

| TYPE OF EXCHANGE | SEPARATION FACTOR |
|---|---|
| H | 1.1–1.6 |
| Na | 0.6–0.8 |
| K | 1.8–3.0 |
| Rb | 2.5–3.5 |
| Ca | 1.17–1.5 |
| Ba | 1.6–2.1 |

TABLE 2

Selectivity ranges at ambient temperature for variously exchanged X zeolites.

| TYPE OF EXCHANGE | SEPARATION FACTOR |
|---|---|
| Na | 1.4–2 |
| K | 1.15–1.6 |
| Ca | 1.8–3.0 |

The selectivity values vary little as the temperature varies, and in spite of the phase passage, the data reported in Tables 1 and 2 can be extended to behaviour in the vapour phase with limited variation, as will be shown in the examples given hereinafter.

In addition to selectivity, the loading capacity of the tested zeolites also varies little in passing from the liquid phase to the vapour phase. For example, in the liquid phase there is generally an adsorption of $1.5-1.7 \times 10^{-3}$ moles per g of zeolite, whereas in the vapour phase this value falls to $1.3-1.5 \times 10^{-3}$ moles/g of zeolite.

It is important to note that in order to attain the objects of the invention, the value of the equilibrium constant Keq of the individual deadsorbents must lie around ±40% of the Keq value of the individual isomer. For comparison purposes, the Keq values must all be evaluated at the same temperature and pressure.

The two deadsorbents are fed to the separation column pure in predetermined succession.

In order to better understand the characteristics and advantages of the invention, some non-limiting embodiments are described hereinafter with reference to the two figures of the accompanying drawings.

These figures show diagrams relating to the variation in the composition of the parachlorotoluene isomer (dashed curve) and the composition of the orthochlorotoluene isomer (continuous curve) at the column outlet. The ordinate axis represents concentration and the abscissa axis represents time. The concentrations are expressed as molar fractions, and the time is expressed in hours.

EXAMPLE 1

Separation of parachlorotoluene and orthochlorotoluene from a mixture of ortho and parachlorotoluene in equal parts. A stream deriving from 198 cm³/hour of a liquid 1:1 molar ratio mixture or ortho and parachlorotoluene, a stream of toluene, and a stream of monochlorobenzene are fed in the vapour phase at 230° C. and 1 atmosphere, in cyclic sequence for 20 minutes, for 10 minutes and for 60 minutes respectively, to a steel column of inner diameter 2 cm and length 660 cm disposed in a temperature-controlled oven and filled with 1050 g of zeolite X in the form of extruded ⅛" pellets in which the initially present sodium had been exchanged with calcium to the extent of more than 98%. The entire system was temperature controlled at 230° C. The composition of the emergent mixture, determined by gas chromatography, is shown in FIG. 1.

It can be seen that the parachlorotoluene leaves first, and is considerably enriched. The adsorption of orthochlorotoluene, parachlorotoluene, toluene and monochlorobenzene obeys a Langmuir isotherm is a very satisfactory manner. For the type of zeolite described, Table 3 shows the values of $\Gamma_i^\infty$ and Keq$_i$, determined by processing the data of FIG. 1.

TABLE 3

Data relating to adsorption on zeolite X exchanged with calcium to the extent of more than 98%, the data being obtained from break-through curves. Temperature 230° C., pressure 1 atmosphere.

| orthochlorotoluene | $1.25-1.35 \times 10^{-3}$ | moles/g |
|---|---|---|
| parachlorotoluene | $1.20-1.30 \times 10^{-3}$ | moles/g |
| toluene | $1.25-1.35 \times 10^{-3}$ | moles/g |
| monochlorobenzene | $1.36-1.50 \times 10^{-3}$ | moles/g |
| Keq orthochlorotoluene | $1.5 \times 10^{+3}$ | liters/mole |
| Keq parachlorotoluene | $1.0 \times 10^{+3}$ | liters/mole |
| Keq toluene | $2.1 \times 10^{+3}$ | liters/mole |
| Keq monochlorobenzene | $.7 \times 10^{+3}$ | liters/mole |

EXAMPLE 2

Separation of parachlorotoluene and orthochlorotoluene from a 9:1 molar mixture of para and orthochlorotoluene.

Figure 2:
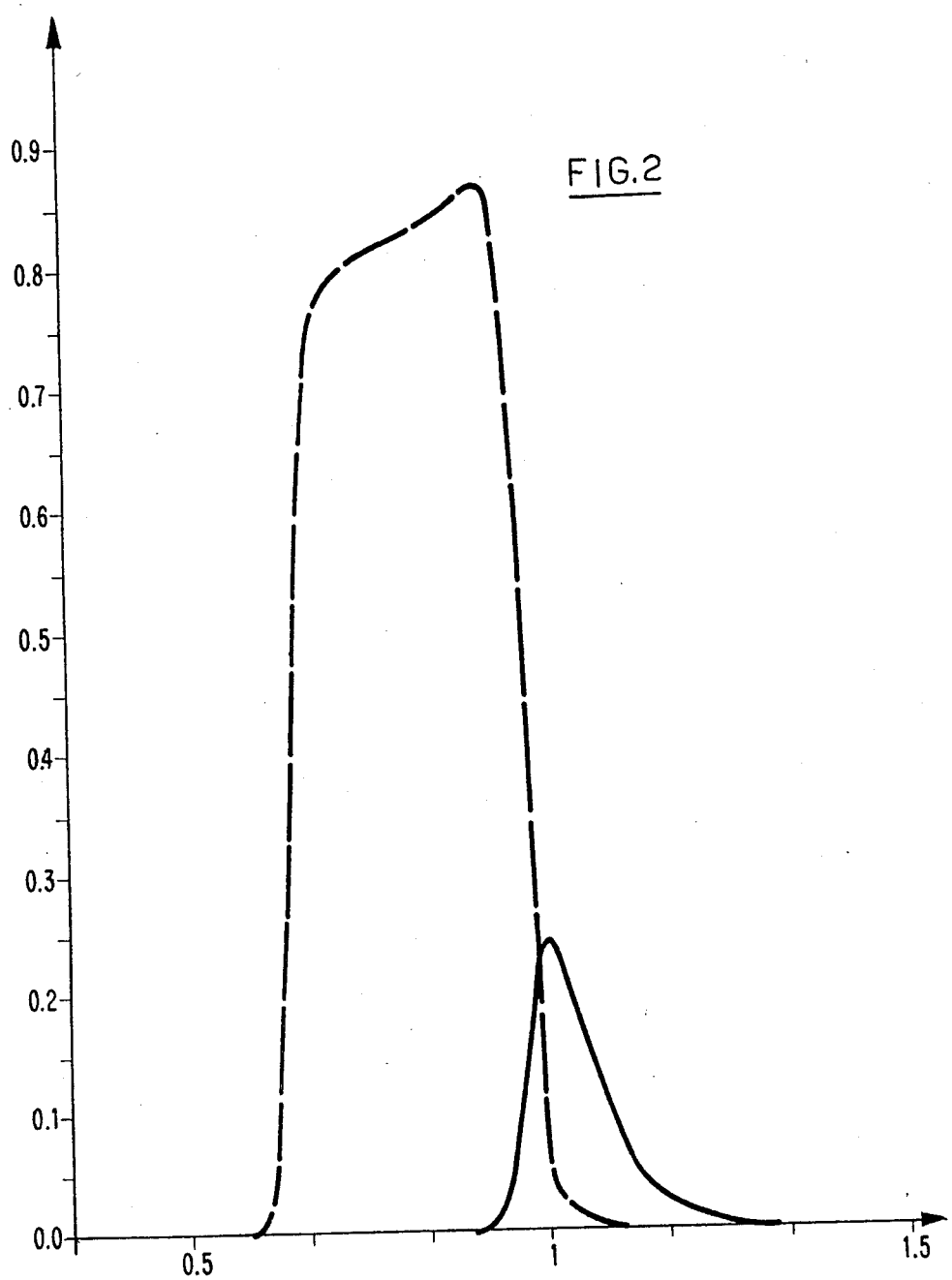

The column of Example 1 is fed in the vapour phase, at 230° C. and 1 atmosphere, with a stream deriving from 190 cm³/h of a liquid 9:1 molar mixture of para and orthochlorotoluene for 20 minutes, a stream of toluene for 20 minutes, and a stream of monochlorobenzene for 40 minutes in cyclic sequence. The entire assembly is temperature controlled at 230° C. The composition of the emergent mixture determined by gas chromatography is shown in FIG. 2. The values of the adsorption constants are shown in Table 3.

The process according to the invention enables the aforesaid objects to be effectively attained. In order to quantify the main advantage of the invention compared with separation of the same type of isomer mixture in which only one deadsorbent is used instead of two, it should be noted that in order to obtain 99% purity of both separated isomers, 250 kg zeolite/kg of mixture must be used in the case of a single deadsorbent, whereas with the process according to the invention 80 kg zeolite/kg of fed mixture are sufficient.

The invention also relates to a plant for carrying out the aforesaid process.

Figure 3:
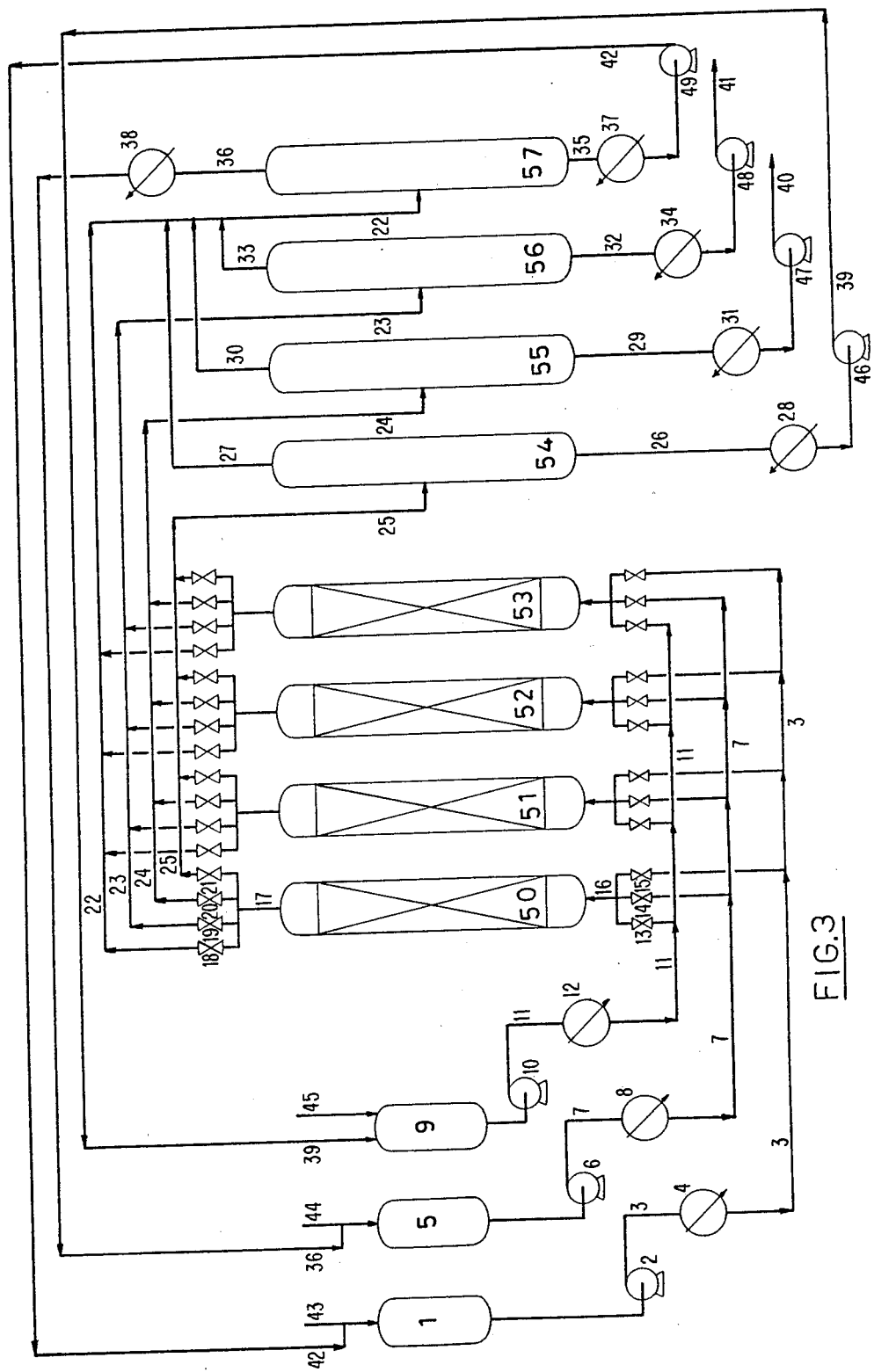

The flow diagram of a plant according to the invention is shown in FIG. 3 by way of non-limiting example.

With reference to FIG. 3, a fresh mixture of ortho and parachlorotoluene to be separated, and originating from the synthesis section through a line 45, is added in the vessel 9 to a non-separated recycle fraction originating from the distillation section by way of a condenser 28, a pump 46 and a line 39. The mixture is then fed by a pump 10 through an evaporator 12 and a line 11, to the separation plant composed of columns 50, 51, 52, 53 containing solid absorbent of absolutely identical behaviour, the number of columns being greater than one so as to be able to treat a constant throughput.

The cyclic behaviour of a single column, for example column 50 is described hereinafter, but this bevhaviour is absolutely identical for the other columns.

The column 50 receives the mixture to be separated by way of the line 11, a valve 13 and a line 16. The valves 14 and 15 remain closed. Through a line 7, the valve 14 and the line 16, the column subsequently receives the first deadsorbent, namely toluene, from a vesel 5 to which it arrives through a line 36 from the recovery and distillation section, plus any necessary make-up through a line 44, the toluene being vaporised in 8. The valves 13 and 15 remain closed. In the last stage of the cycle, the column receives monochlorobenzene through the line 16, the valve 15 and the line 3, this monochlorobenzene being pumped by the pump 2 from the vessel 1 to which it is fed from a distillation section 57 by way of a condenser 37, pump 49 and line 42. The valves 13 and 14 are closed.

Four fractions are obtained at the other end of the column 50 by way of a line 17 and valves 18, 19, 20 and 21, of which only one is open, these fractions being fed through lines 22, 23, 24, 25 to the section in which they are separated from the deadsorbents and the deadsorbents are separated from each other, this being carrid out in distillation columns 54, 55, 56 and 57. The first fraction, collected through the valve 20 and line 24, contains parachlorotoluene in high concentration. It is separated in 55 from the mixture of toluene and monochlorobenzene, these latter being fed as overhead product through lines 30 and 22 to their separation stage. Pure parachlorotoluene is obtained at the bottom of the column and is cooled at 31, then fed by the pump 47 and line 40 to the storage tank. The third fraction containing orthochlorotoluene at high concentration is obtained in a like manner and is fed to the column 56, from which it is recovered pure in the liquid state by way of the line 32 and heat exchanger 34, and is fed by the pump 48 and line 41 to storage. The second section containing insufficiently separated ortho and parachlorotoluene is recovered by way of the valve 21 and line 25 and is separated from the deadsorbents in column 54, then condensed in 28, and fed by the pump 46 and line 39 to the feed vessel 9. As a modification, this section can be recycled to the column directly without the two deadsorbents being separated from it.

The deadsorbent mixture, separated from the isomers in columns 54, 55 and 56, is fed by way of lines 27, 30 and 33 to line 22 arriving from the column 50 by way of the valve 18, the deadsorbent mixture then being separated into its individual constituents in column 57. These are recycled through lines 42 and 36 to the feed vessels 1 and 5.

We claim:

1. A process for separating mixed monochlorotoluene isomers, comprising a first stage of adsorption carried out by passing said mixture through at least one column filled with a zeolite, characterized by comprising a second stage of deadsorption from said zeolite carried out by passing two deadsorbents in succession in the vapour phase through the column, equilibrium constants of the deadsorbents, measured from the breakthrough curves, lying within ±40% of the equilibrium constants of the isomers to be separated.

2. A process as claimed in claim 1, characterized in that said two deadsorbents are toluene and monochlorobenzene.

3. A process as claimed in claim 1, characterized in that said zeolite is a wide-pore faujasite, either of X type in which the cation present has been exchanged with calcium to the extent of more than 98%, or of Y type in which the cation present has been exchanged with potassium to the extent of more than 98%.

* * * * *